United States Patent [19]

Ohsuga et al.

[11] Patent Number: 4,814,045
[45] Date of Patent: Mar. 21, 1989

[54] METHOD FOR DETECTING AIR-FUEL RATIO

[75] Inventors: Minoru Ohsuga; Yoshishige Oyama, both of Katsuta, Japan

[73] Assignee: Hitachi, Ltd., Tokyo, Japan

[21] Appl. No.: 92,222

[22] Filed: Sep. 2, 1987

[30] Foreign Application Priority Data

Sep. 10, 1986 [JP] Japan ................................ 61-211642

[51] Int. Cl.[4] ............................................ G01N 27/46
[52] U.S. Cl. ..................................... 204/1 T; 204/425; 204/427
[58] Field of Search .......................... 204/1 S, 421–429

[56] References Cited

U.S. PATENT DOCUMENTS

| | | | |
|---|---|---|---|
| 4,294,668 | 10/1981 | Young | 204/424 |
| 4,356,065 | 10/1982 | Dietz | 204/1 S |
| 4,437,971 | 3/1984 | Csanitz et al. | 204/428 |
| 4,543,176 | 9/1985 | Harada et al. | 204/425 |
| 4,629,535 | 12/1986 | Oyama et al. | 204/427 |

*Primary Examiner*—T. Tung
*Attorney, Agent, or Firm*—Fay, Sharpe, Beall, Fagan, Minnich & McKee

[57] ABSTRACT

The oxygen is supplied the diffusion resistor (3) for a specified period of time during operation so as to oxidize the contaminate particles (6) adhering to the diffusion resistor (3), when the solid electrolyte (2) is impressed a voltage by the power source (8) so as to move the oxygen from the solid electrolyte (2) to the diffusion resistor (3). For a specified period during operation, such as during a certain period after ignition key is switched on, during the rich air-fuel ratio operation, during idling, or during warmup operation at starting, the oxygen is supplied to the diffusion resistor (3). It is possible to provide the air-fuel ratio sensor (1) which has no output variation due to degradation over long period of use by removing the contaminated particles (6).

5 Claims, 13 Drawing Sheets

METHOD FOR DETECTING AIR-FUEL RATIO

BACKGROUND OF THE INVENTION

1. Field of the Invention

The present invention relates to an air-fuel ratio sensor which measures the air-fuel ratio of the fuel mixture in internal combustion engines from exhaust gas and more specifically to an air-fuel ratio sensor for detecting the air-fuel ratio of the fuel mixture in internal combustion engines from exhaust gas comprising an oxygen ion conductive solid electrolyte, a diffusion resistor, a heater and an electrode. The air-fuel ratio sensor in the present invention can prevent variations in the sensor output with the passage of time due to clogging of the diffusion resistor.

2. Description of the Prior Art

The conventional air-fuel ratio sensor, for example as disclosed in the Japanese Patent Application Laid-Open No. 57050/1983, has its sensor output characteristic corrected according to the detected value when the atmospheric air is measured. However, the above-mentioned conventional air-fuel ratio sensor shows no positive means to prevent the sensor output variations that may occur with the elapse of time.

The above mentioned conventional air-fuel ratio sensor does not propose a means to remove contaminate particles such as carbon, sulfer, dust etc., adhering, to the diffusion resistors, but only considers a means for correcting the sensor output of the air-fuel ratio sensor. So, the conventional air-fuel ratio sensor has a problem in keeping the precision of the air-fuel ratio over a long period of time.

With the conventional system, it is in practice difficult to make sensor output corrections with good accuracy because the sensor output characteristic for the air-fuel ratio is not linear.

SUMMARY OF THE INVENTION

An object of the present invention is to provide an air-fuel ratio sensor wherein the contaminated particles adhering to the diffusion resistor of the air-fuel ratio sensor can be removed.

Another object of the present invention is to provide an air-fuel ratio sensor wherein the sensor output of the air-fuel ratio sensor does not change after a long period of use.

The above objects of the present invention can be achieved by supplying oxygen to the diffusion resistor of the air-fuel ratio sesor for a specified period of time during operation.

In accordance with the present invention, the air-fuel ratio sensor for detecting the air-fuel ratio of the fuel mixture in internal combustion engines from exhaust gas comprises an oxygen ion conductive solid electrolyte and a diffusion resistor.

A means to supply oxygen to the diffusion resistor for a specified period of time during operation is provided so as to oxidize contaminated particles adhering to the diffusion resistor.

The time period in which the oxygen is supplied to the diffusion resistor is a rich fuel mixture operation period in which the air-fuel ratio is smaller than a theoretical air-fuel ratio.

The oxygen is supplied for a specified period to the diffusion resistor when the output obtained by measuring the atmospheric air which has reached the air-fuel ratio sensor during the fuel cut-off time is below a specified value.

The air-fuel ratio measuring operation and the operation for supplying the oxygen to the diffusion resistor are performed alternately for a specified duration each.

The amount of the oxygen supplied to the diffusion resistor is greater than that required for reaction with unburnt gas components in the diffusion resistor.

The operation for supplying the oxygen to the diffusion resistor is performed for a specified period of time repeatedly during the normal measuring operation.

The time period during which the oxygen is supplied to the diffusion resistor is the one in which the solid electrolyte is heated to 600° C. to 900° C. by the heater.

The operation for supplying the oxygen to the diffusion resistor is performed when a drift in the air-fuel ratio sensor output, which is detected by forcibly changing the air-fuel ratio by a specified amount during the engine idling, is determined to be greater than a certain value.

With the diffusion resistors supplied with the oxygen, the air-fuel ratio sensor of the present invention can oxidize and remove the contaminate particles such as carbon, sulfur, dust, etc., adhering to the diffusion resistor and thereby prevent the sensor output variation that would otherwise occur with the elapse of time.

According to the present invention, it is possible to provide an air-fuel ratio sensor that has no output variation due to degradation over a long period of use by removing the contaminated particles that will lead to the clogging of the diffusion resistor.

DETAILED DESCRIPTION OF THE EMBODIMENTS

Figures 1, 2, 3:
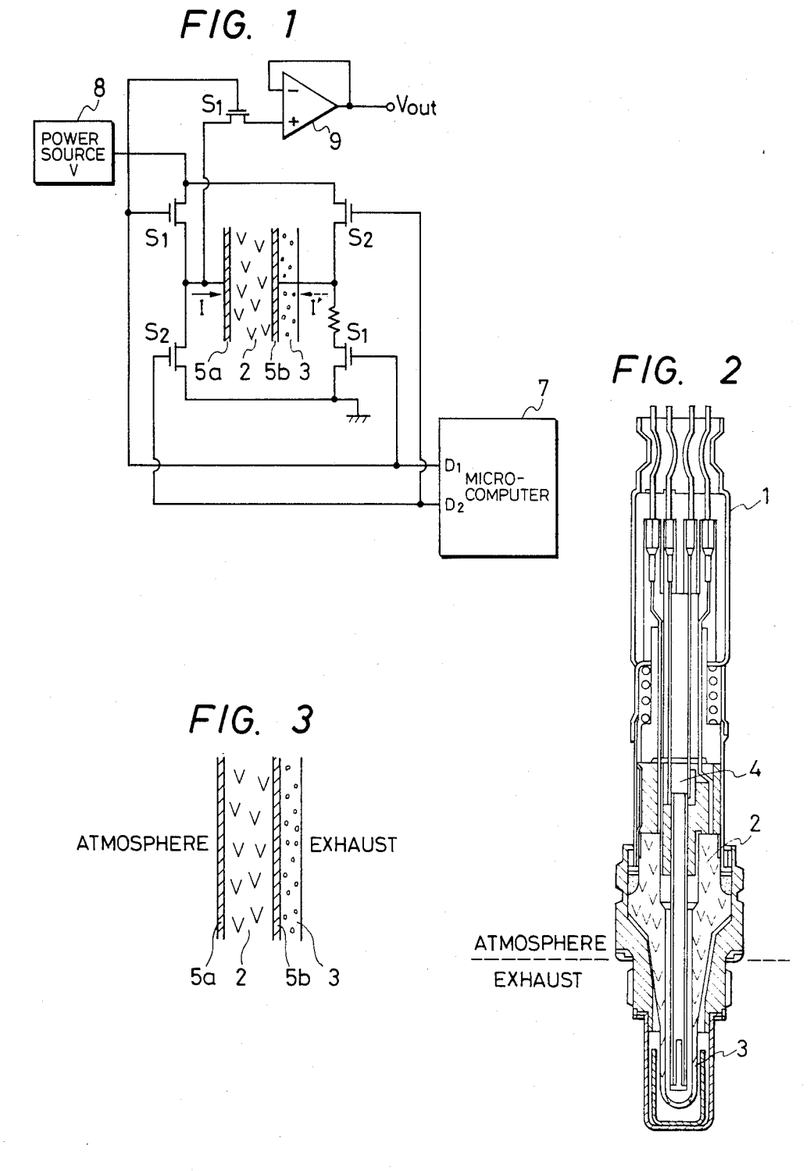
FIG. 1 shows a circuitry having the air-fuel ratio sensor of one embodiment according to the present invention.
FIG. 2 shows the cross-sectional structure of the air-fuel ratio sensor according to the present invention.
FIG. 3 shows the enlarged cross-sectional structure of the surrounding portion of the diffusion resistor of the air-fuel ratio sensor according to the present invention.

One embodiment of an air-fuel ratio sensor according to the present invention is described in the following. FIG. 2 shows the structure of the air-fuel ratio sensor 1. The air-fuel ratio sensor 1 comprises an oxygen-ion conductive solid electrolyte 2, a porous diffusion resistor 3, a heater 4, and an atmosphere side electrode 5a and an exhaust side electrode 5b respectively. FIG. 3 is an enlarged view of a surrounding portion of the diffusion resistor 3.

The solid electrolyte 2 is heated up to 600° C. to 900° C. by the heater 4. External atmospheric air is introduced into the interior of the heater 4 of the solid electrolyte 2 and the exhaust gas is introduced to the outside of the heater 4.

Figure 4:
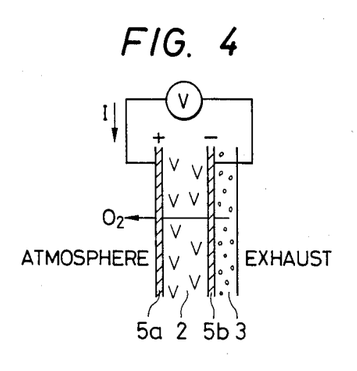
FIG. 4 shows the operating principle of the air-fuel ratio sensor according to the present invention.

As shown in FIG. 4, a voltage V is impressed so that the atmosphere side electrode 5a is positive and the exhaust side electrode 5b is negative. The voltage V causes the current I to flow in the direction of the solid arrow, moving the oxygen ($O_2$) toward the atmosphere side. Then, the diffusion resistor 3 prevents the diffusion of oxygen and the current I is called a limit current value which is proportionate to the concentration of oxygen in the discharged gas. This air-fuel ratio sensor 1 measures the limit current value I. The relationship between the current I and the theoretical air-fuel ratio λ is shown as a solid line $A_1$ in FIG. 6. Here, the theoretical air-fuel ratio λ λ=1.0 shows air-fuel ratio (A/F) of 14.7.

Figure 5:
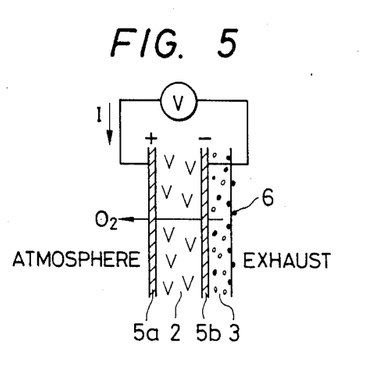
FIG. 5 shows the air-fuel ratio sensor in having contaminating particles.
Figure 6:
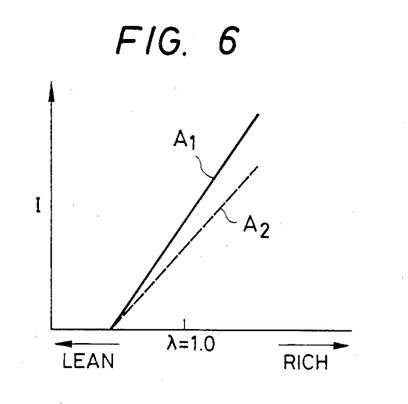
FIG. 6 is a graph showing the relationship between the theoretical air-fuel ratio $\lambda$ and the limit current value I.

In the air-fuel ratio sensor 1 of the above construction, contaminate particles 6, such as carbon, ion, oil, etc. adhere to the diffusion resistor 3 as shown in FIG. 5, the diffusion of oxygen is hindered and the current I falls as shown by a broken line $A_2$ in FIG. 6. Although there is a method for detecting the fall of the current I value and making correction accordingly, since the λ-I characteristic is non-linear it is difficult to make exact correction. Furthermore, the correction of the air-fuel ratio sensor will make the air intake system more complicated.

Considering the above drawbacks with the conventional air-fuel ratio sensor, the present invention prevents the sensor output variations of the air-fuel ratio sensor that would otherwise result from a long period of use, by positively removing the contaminate particles 6.

Figure 7:
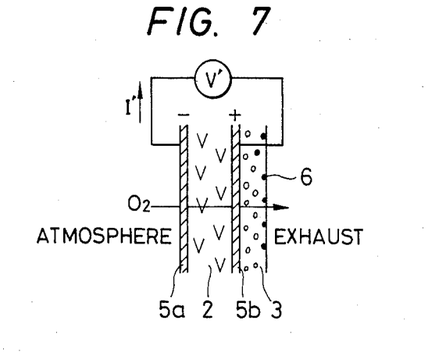
FIG. 7 shows the operating principle of the air-fuel ratio sensor according to the present invention.
Figure 8:
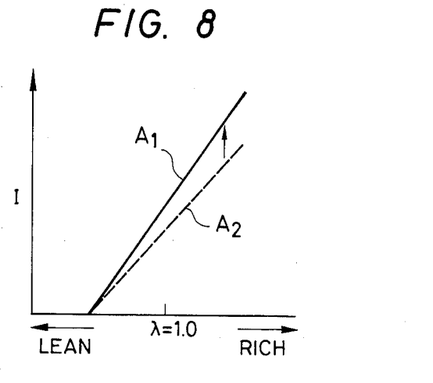
FIG. 8 is a graph showing the relationship between the theoretical air-fuel ratio $\lambda$ and the limit current value I.

FIGS. 7 and 8 show the operating principle of the air-fuel ratio sensor. As shown in FIG. 7, for a certain period during operation a voltage V' is applied so that the atmosphere side electrode 5a is negative and the exhaust side electrode 5b is positive, to cause the oxygen ($O_2$) to move toward the diffusion resistor 3. The solid electrolyte 2 is heated at around 600° C. to 900° C. by the heater 4. The atmosphere side electrode 5a and the exhaust side electrode 5b are formed respectively of (platinum) Pt which has catalytic action.

So the contaminated particles 6 are oxidized by the oxygen ($O_2$) moved to the diffusion resistor 3 which is then cleared of the contaminated particles 6 and is restored to the original condition. The sensor output characteristic of the air-fuel ratio sensor 1, as shown in FIG. 8, is also recovered from the broken line $A_2$ to the solid line $A_1$, the solid line $A_1$ being the sensor output characteristic before it gets contaminated.

With this structure of the air-fuel ratio sensor 1 according to the present invention, it is possible to maintain the initial sensor output characteristic of the air-fuel ratio sensor 1, requiring no sensor output correction.

FIG. 1 shows one embodiment of the air-fuel ratio sensor according to the present invention representing the actual circuitry to realize the above function.

In the circuit diagram shown in FIG. 1, in measuring the air-fuel ratio, a microcomputer 7 causes $D_1$ and $D_2$ to produce ON and OFF signals respectively to turn on the switch $S_1$ and turn off the switch $S_2$. This applies the voltage V to the solid electrolyte 2 causing the current I to flow in the direction of the solid arrow of FIG. 1. The current I is taken out through a buffer amplifier 9 as an output $V_{out}$ which is proportionate to the theoretical air-fuel ratio λ.

Next, for a specified period during operation, such as during a certain period after the ignition key is switched on, during the rich air-fuel ratio operation, during idling, or during warmup operation at starting, the oxygen is supplied to the diffusion resistor 3. In this period the microcomputer 7 uses $D_1$ as an OFF signal and $D_2$ as an ON signal to turn the switch $S_1$ off and switch $S_2$ on. Then voltage V is applied, but since the polarity is opposite to that during the measuring operation, the current I' now flows in the direction of the broken arrow. This causes the oxygen to move toward the diffusion resistor 3 oxidizing the contaminated particles 6.

Figure 9:
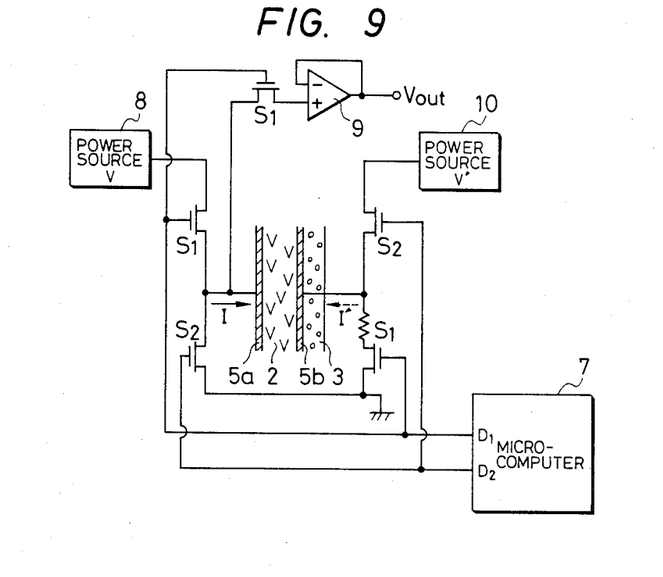
FIG. 9 shows a different circuitry than FIG. 1, having the air-fuel ratio sensor according to the present invention.

FIG. 9 shows another circuitry embodiment according to the present invention. During the measuring operation, $D_1$ is used as ON signal and $D_2$ as OFF signal to apply the voltage V. But for a contaminated particles purge operation in which the oxygen is supplied to the diffusion resistor 3, $D_1$ is used as OFF signal and $D_2$ as ON signal to apply voltage V' of a power source 10. In this case, the current I' flows in the direction of the broken arrow of FIG. 9. In this way, the applied voltage V' is changed for the measuring operation and for the contaminated particles purge operation. During the contaminated particles purge operation, since the oxygen is supplied from the atmosphere, it is effective to make the voltage V' larger than the voltage V.

Figure 10:
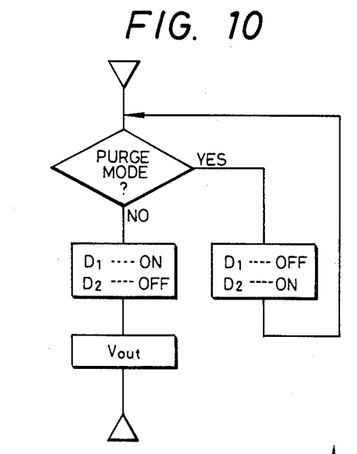
FIG. 10 shows a flow-chart of sensor operating of the air fuel ratio sensor according to the present invention.

FIG. 10 shows the operation flow-chart of one embodiment of the present invention. First, a check is made of whether the air-fuel ratio sensor 1 is in the contaminate particles purge mode or not. When it is not in the contaminate particles purge mode, $D_1$ is used as the ON signal and $D_2$ as the OFF signal to read the value $V_{out}$. When it is in the contaminate particles purge mode, $D_1$ is used as OFF signal and $D_2$ as ON signal to perform the contaminate particles operation. The purge contaminated particles purge mode is put into operation, as mentioned earlier, during a certain period of time after the ignition key was turned on, or during the rich air-fuel ratio operation, or during idling or during warmup operation at starting.

Figure 11:
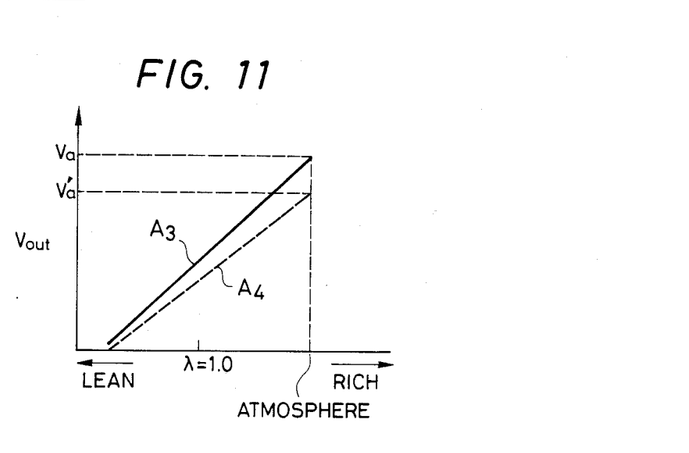
FIG. 11 shows a characteristic of the air-fuel ratio sensor according to the present invention.

Clogging of the diffusion resistor 3 is detected by measuring the atmospheric air that is taken in as a reference gas during a fuel cut-off period. When the diffusion resistor 3 is clogged, the value $V_{out}$ is the value $V'_a$ which is smaller than the initial value of $V_a$ as shown in FIG. 11.

Figure 12:
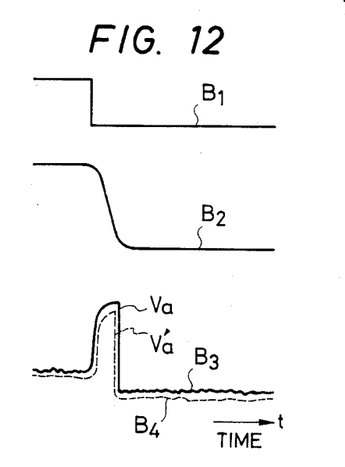
FIG. 12 shows the operation of the contaminated particles purge mode.

FIG. 12 shows the operation of the above case. $B_1$ represents the condition where the throttle valve is rapidly closed cutting off the fuel supply for deceleration. $B_2$ represents the number of engine revolutions, which rapidly drops as the throttle valve is closed. $B_3$ represents the value $V_{out}$ which increases up to a peak value $V_a$ as the fuel is cut off and the atmospheric air reaches the airfuel ratio sensor portion.

If at this time the diffusion resistor 3 is clogged, the $V_{out}$ will be lower as indicated by the dotted characteristic line $B_4$ of FIG. 12 and its peak value will be value $V_a'$ which is lower than value $V_a$ when the atmospheric air reaches the air-fuel ratio sensor portion. When value $V_a'$ is measured, the clogging of the diffusion resistor 3 is detected.

Figure 13:
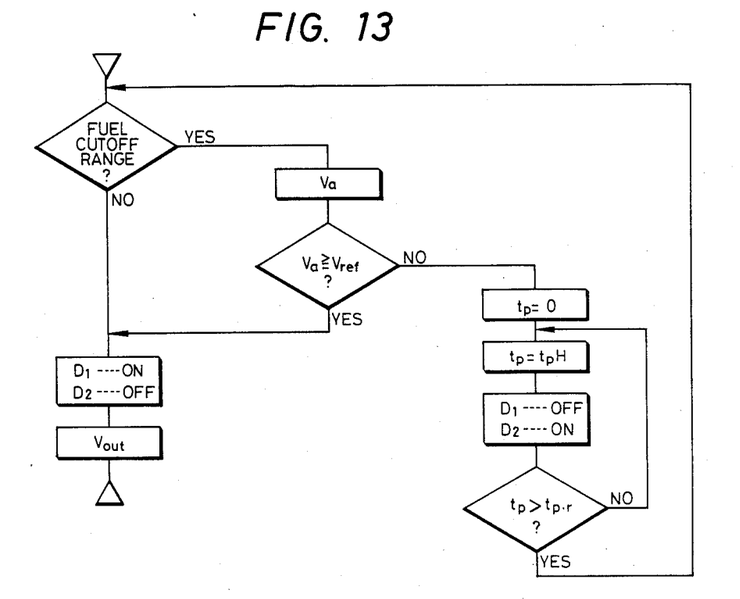
FIG. 13 shows a flow-chart of sensor operation of the air-fuel ratio sensor according to the present invention.

FIG. 13 shows the flow-chart of clogging detection operation. The circuit may be formed as shown in FIG. 1 or FIG. 9. When the fuel is cut off, the value $V_{out}$ when the atmospheric air arrives at the air-fuel ratio sensor 1, or the value $V_a$, is read first to check whether the value $V_a$ is greater than a specified value $V_{ref}$. If the value $V_a$ is found to be not greater than the specified value $V_{ref}$, *the air-fuel ratio sensor enters the contaminated particles purge mode.*

During the contaminate particles purge mode, ocurring for time tp $D_1$ line is deenergized and $D_2$ line energized to flow the oxygen toward the diffusion resistor 3 until tp is greater than a specified reference time tp.r. When on the other hand the engine operation is not in the fuel-cut zone or $V_a$ $V_{ref}$, then the air-fuel ratio sensor 1 enters the normal measuring mode in which $D_1$ is energized and $D_2$ deenergized to read the value $V_{out}$.

With the above operation, it is possible to detect clogging and thereby cause the air-fuel ratio sensor 1 to enter the contaminate particles purge mode only when the clogging occurs.

Figure 14:
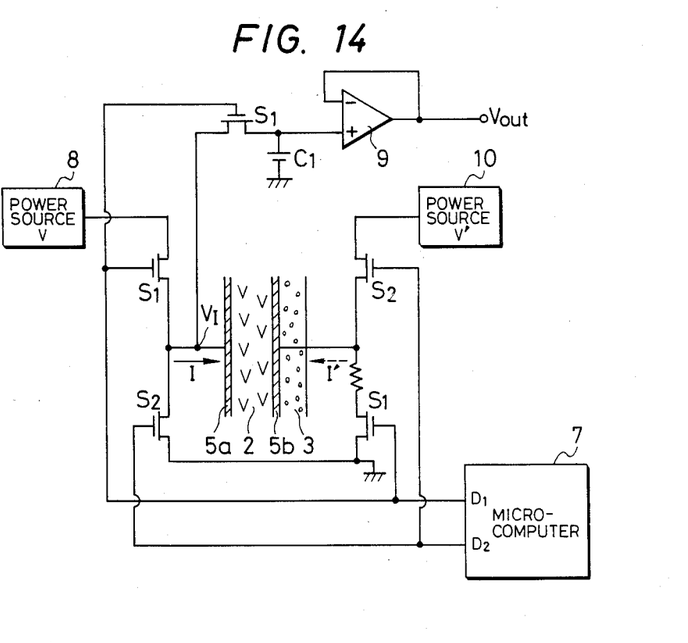
FIG. 14 shows a circuitry having the air-fuel ratio sensor of a further embodiment according to the present invention.
Figure 15:
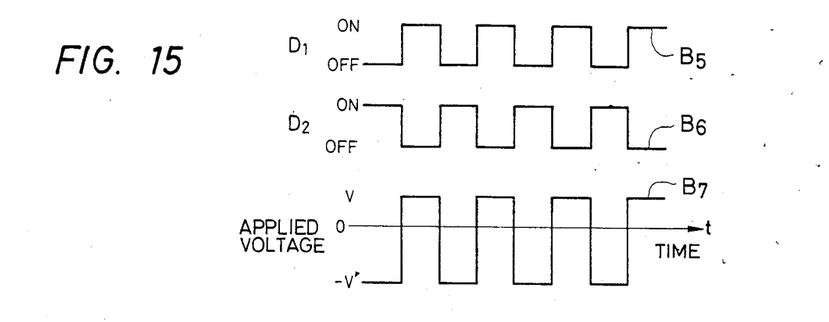
FIG. 15 shows a flow-chart of sensor operation of the air-fuel ratio sensor according to the present invention.

FIGS. 14 and 15 show still another embodiment of the present invention in which the contaminated particles purge mode and the measuring contaminated particles purge mode are performed alternately.

As shown in FIG. 15, $D_1$ and $D_2$ are alternately turned on and off for a certain period of time as shown in periodic lines $B_5$ and $B_6$ so that the voltage applied to the solid electrolyte 2 alternates between the value V and the value V' as shown in periodic line B. When the voltage V' is applied, the air-fuel ratio sensor 1 is in the contaminate particles purge mode. In this case, it is necessary to hold in a capacitor $C_1$ the voltage $V_I$ of the atmosphere side electrode 5a during the measuring mode to put it out as the value $V_{out}$ through the amplifier 9.

The air-fuel ratio sensor 1 of the present invention permits the contaminate particles purge mode to be performed preventing the diffusion resistor 3 from getting clogged so that the air-fuel ratio sensor 1 maintains its initial performance without any degradation in output with the passage of time.

Figure 16:
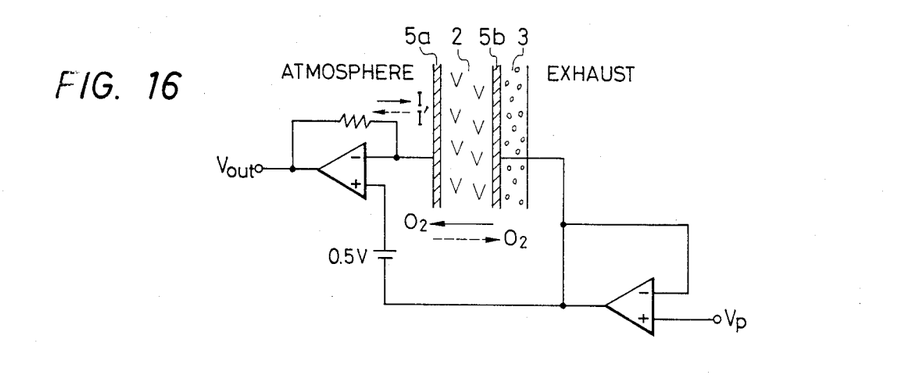
FIG. 16 shows the operating process of the air-fuel ratio sensor according to the present invention.
Figure 17:
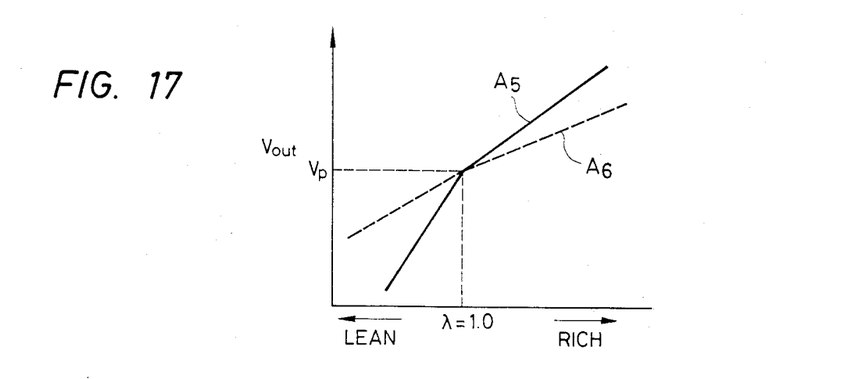
FIG. 17 is a graph showing the relationship between the theoretical air-fuel ratio λ and the $V_{out}$ characteristics.

FIGS. 16 and 17 show the structure and working principle of a wide range air-fuel ratio sensor 1 capable of measuring a wide range of air-fuel ratio from the lean zone to the rich zone.

The electrode 5b on the exhaust side is impressed with a voltage $V_p$ as a potential ground and the other electrode 5a on the atmosphere side is applied with a voltage 0.5V higher than the voltage $V_p$. The voltages at each electrode 5a and 5b are expressed as follows. When the fuel is lean, $$\text{electrode } 5a \text{ (atmosphere side)} \ldots V_p+0.5 \text{ (V)} \ldots \quad (1)$$

$$\text{electrode } 5b \text{ (exhaust side)} \ldots \ldots V_p \text{ (V)} \ldots \quad (2)$$

When it is rich, an electromotive force E (approx. 1.0V) is generated in the solid electrolyte 2 and the electrode voltage will be $$\text{electrode } 5a \text{ (atmosphere side)} \ldots V_p+0.5 \text{ (V)} \ldots \quad (3)$$

$$\text{electrode } 5b \text{ (exhaust side)} \ldots \ldots V_p+E \text{ (V)} \ldots \quad (4)$$

In other words, when the fuel is lean, $$\text{voltage on atmosphere side} > \text{voltage on exhaust side} \ldots \quad (5)$$

So the current I flows in the direction of the solid arrow of FIG. 16 and the oxygen moves from the exhaust side to the atmosphere side.

When the fuel mixture is rich, $$\text{voltage on atmosphere side} < \text{voltage on exhaust side} \ldots \quad (6)$$

Then the current I flows in the direction of the dotted arrow of FIG. 16 and the oxygen moves from the atmosphere side to the exhaust side. The oxygen ($O_2$) reacts with the unburnt components such as CO, HC, $H_2$ contained in the exhaust gas, so that the amount of oxygen, i.e., current I, is proportionate to the air-fuel ratio (A/F) in the rich fuel mixture zone.

FIG. 17 shows the $V_{out}$ characteristic of the above embodiment. The output $V_{out}$ is the value $V_p$ (potential ground) when $\lambda=1.0$ as shown by a solid line $A_5$ and, in the lean mixture zone, is greater than the value $V_p$ and in the rich mixture zone is smaller than the value $V_p$.

When the diffusion resistor 3 gets clogged with carbon particles, the $V_{out}$ characteristic will change to the one indicated by a broken line $A_6$.

Figure 18:
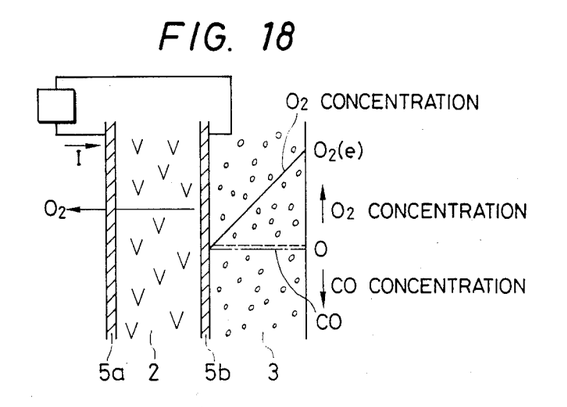
FIG. 18 shows the operating process of the air-fuel ratio sensor showing the oxygen distribution according to the present invention.
Figure 19:
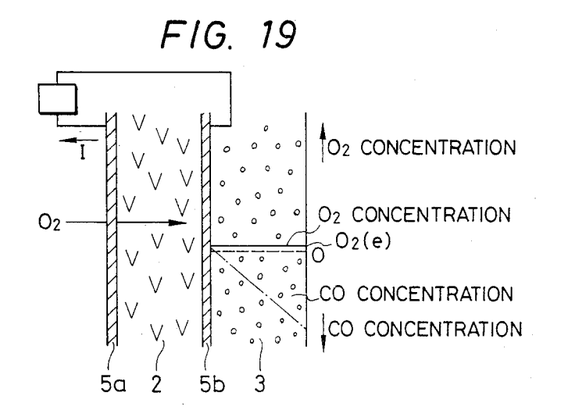
FIG. 19 shows the operating process of the air-fuel ratio sensor showing the oxygen distribution according to the present invention.

FIGS. 18 and 19 show the oxygen concentration distribution in the diffusion resistor 3 during the measuring mode.

FIG. 18 represents the case of lean mixture operation in which the oxygen concentration in the diffusion resistor 3 on the exhaust side is equal to that in the exhaust gas $0_2(e)$. The current I is controlled so that the oxygen concentration in the diffusion resistor 3 on the exhaust side electrode 5b is almost zero during the measuring mode. Thus the oxygen concentration distribution is as shown in FIG. 18. In such a lean fuel mixture condition, there is ample oxygen in the diffusion resistor 3 which oxidizes carbon, if any, adhering to the diffusion resistor 3 thus keeping it free from clogging.

FIG. 19 shows the oxygen concentration distribution in the rich fuel mixture condition. On the exhaust side in the diffusion resistor 3, there are unburnt components (e.g., CO). On the exhaust side electrode 5b, it is controlled during the metering mode so that the oxygen ($O_2$) supplied from the solid electrolyte 2 reacts with CO to make the carbon monoxide (CO) concentration zero. Thus, the oxygen ($O_2$) and carbon monoxide (CO) concentrations are as shown in FIG. 19. Since there is carbon monoxide (CO) in the diffusion resistor 3, the oxygen ($O_2$) concentration becomes zero, that is, there is no oxygen.

Therefore, when carbon particles adhere to the diffusion resistor 3, they cannot be oxidized and thus remain attached to it. As the amount of carbon adhering to the diffusion resistor 3 increases, the characteristic deteriorates as shown by the dotted line of FIG. 19.

Figure 20:
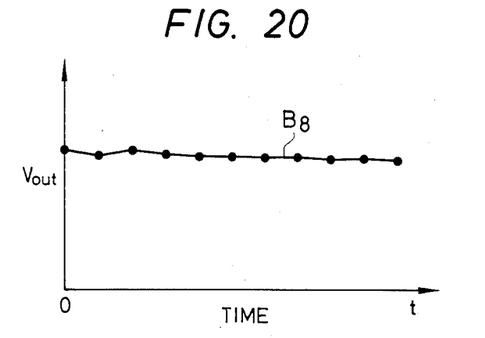
FIG. 20 shows a characteristic obtained from an experiment at the lean condition.
Figure 21:
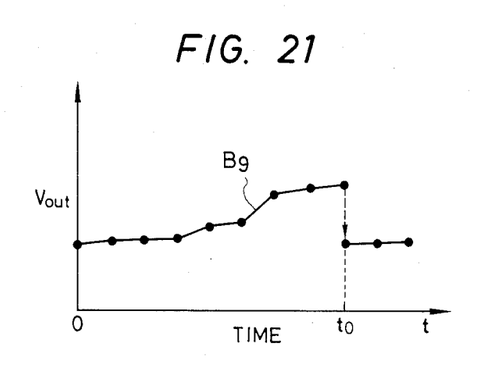
FIG. 21 shows a characteristic obtained from an experiment at the rich fuel condition.

FIGS. 20 and 21 show the result of an experiment for removing the carbon. FIG. 20 shows the $V_{out}$ characteristics of the air-fuel ratio sensor 1 with respect to time as shown in a line $B_8$ when the engine is run with the fuel mixture kept at a certain lean ratio. There is no drift of the air-fuel ratio sensor 1 observed.

FIG. 21 shows the $V_{out}$ characteristics of the air-fuel ratio sensor 1 with respect to time as shown in a line $B_9$ when the engine was run with the fuel mixture fixed at a certain rich air-fuel ratio. The air-fuel ratio sensor output $V_{out}$ increased with the passage of time, a drifting phenomenon. This is caused by carbon adhering to the diffusion resistor 3. At a point with the passage of the time $t_0$ to where a remarkable drift was observed, the fuel mixture was returned to the lean air-fuel ratio for a specified period of time and then changed to the rich air-fuel ratio. This resulted in the $V_{out}$ characteristics recovering to the initial value thus enabling the correct measurement of the air-fuel ratio.

This means that if there is the oxygen in the diffusion resistor 3 or the oxygen is supplied from time to time, the clogging of diffusion resistor 3 can be prevented. This is because the air-fuel ratio sensor 1 is kept at high temperatures between 600° and 900° C. and because the oxygen in the diffusion resistor 3 oxidizes the carbon attaching to it.

Instead of temporarily returning the fuel mixture to a lean air-fuel ratio while the engine is running with rich fuel mixture, the inventors of the present invention invented a method in which the diffusion resistor 3 itself supplies the oxygen.

Figure 22:
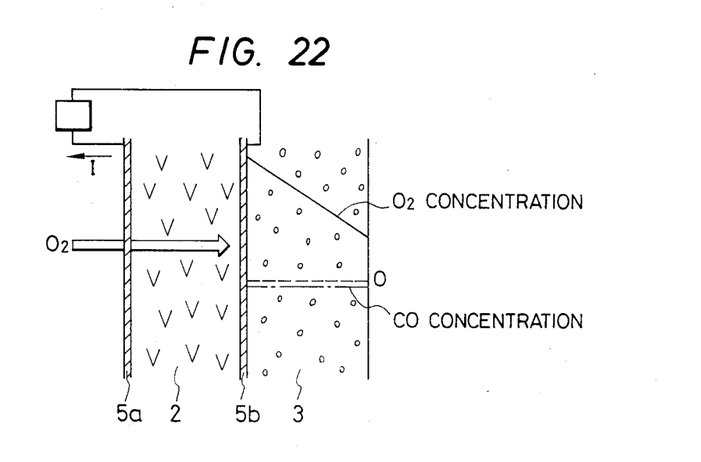
FIG. 22 shows the operating process of the air-fuel ratio sensor showing the oxygen contaminate distribution of a still further embodiment according to the present invention.

FIG. 22 shows the oxygen concentration distribution in the rich fuel condition when the current I is made to flow in the direction of the arrow to forcibly cause the oxygen ($O_2$) to move toward the diffusion resistor 3. Since the oxygen is supplied from the atmosphere side, any desired amount can be supplied by the current I.

Supplying the oxygen in quantity large enough to react with the carbon monoxide (CO) in the rich fuel mixture condition results in the oxygen ($O_2$) concentration distribution within the diffusion resistor 3 as shown in FIG. 22. Since the oxygen exists in the diffusion resistor 3, any carbon adhering to the diffusion resistor 3 is oxidized by oxygen at high temperature, thus clearing the diffusion resistor 3 of carbon. In this way, during the rich fuel mixture operation, the oxygen is made to flow toward the diffusion resistor 3 to remove clogging carbon.

Figure 23:
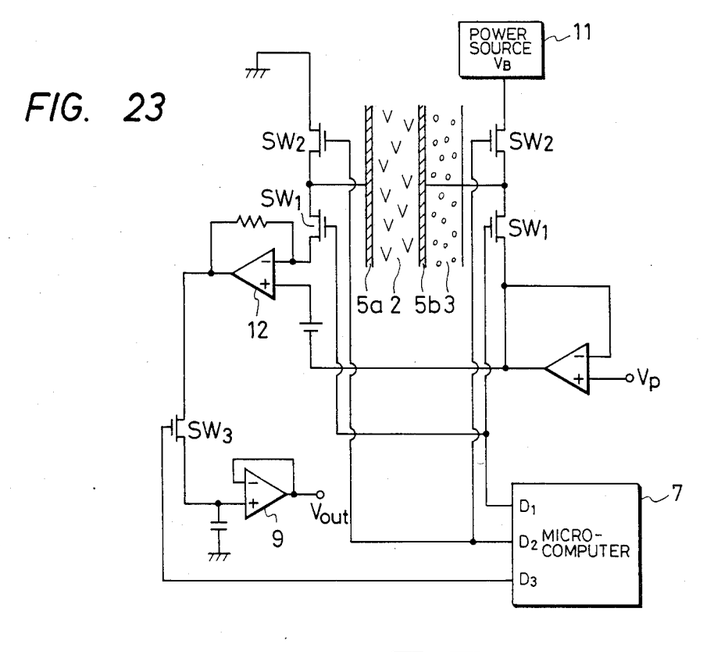
FIG. 23 shows a circuitry having the air-fuel ratio sensor of a further embodiment according to the present invention.
Figure 24:
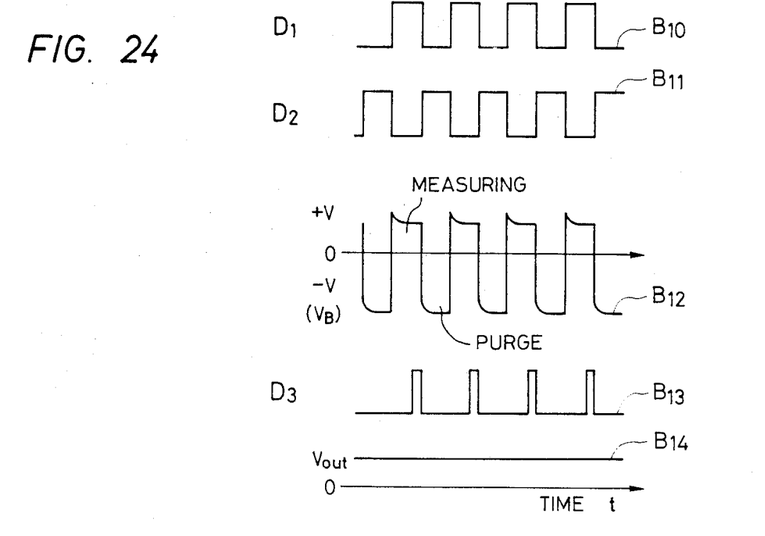
FIG. 24 shows various waveforms of signals during sensor operation according to the present invention.
Figure 25:
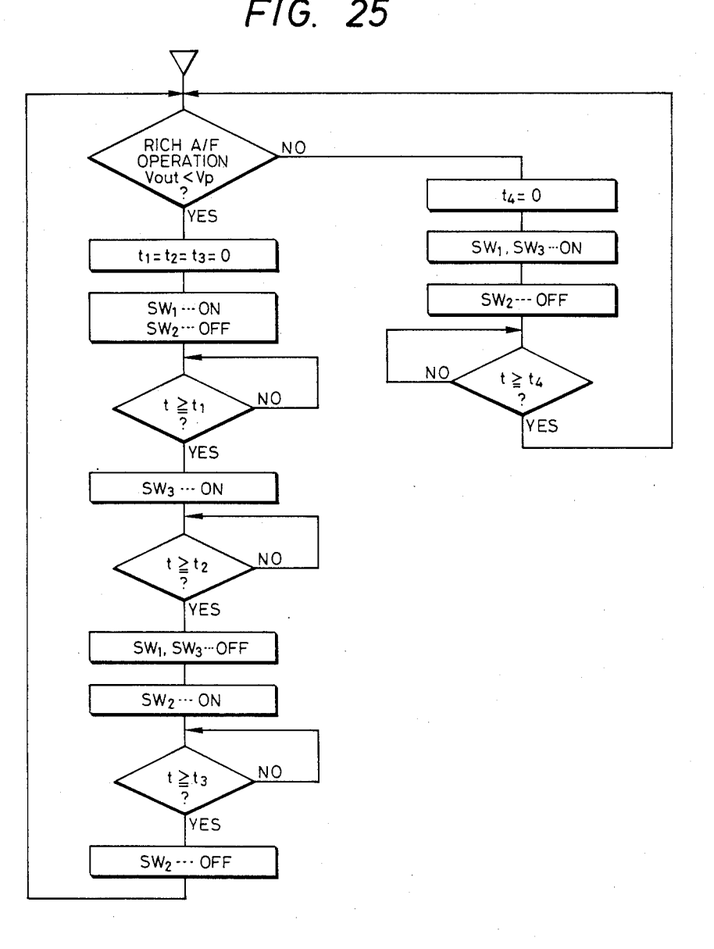
FIG. 25 shows a flow-chart of sensor operation of the air-fuel ratio sensor according to FIG. 23 of the present invention.

FIG. 23 shows one embodiment of the present invention to realize the above technique. FIG. 24 shows the operation waveforms $B_{10}$, $B_{11}$, $B_{12}$, $B_{13}$ and $B_{14}$ at each part of the air-fuel ratio sensor 1. FIG. 25 shows the flow-chart of the air-fuel ratio sensor operation. First, a check is made to determine whether the engine is running with the rich fuel mixture.

When the value $V_{out}$ is smaller than the value $V_p$ or the fuel mixture is rich, the ON signal from $D_1$ turns the switch $SW_1$ on and the OFF signal from $D_2$ turns the switch $SW_2$ off. Then, the air-fuel ratio sensor 1 waits a time period of $t_1$ to avoid being affected by a voltage surge phenomena that would occur after switching and then turns on the switch $SW_3$ by the ON signal from $D_3$, outputting as the value $V_{out}$ the output of the amplifier 12 through the sample and hold circuit 9.

With further elapse of time period ($t_2$-$t_1$), the switch $SW_1$ and the switch $SW_3$ are turned off and the switch $SW_2$ turned on to cause a certain amount of oxygen to flow toward the diffusion resistor 3 by the value $V_B$ and thereby oxidize carbon. Then, the switch $SW_2$ is turned off to repeat the above process.

During the lean fuel mixture ratio, the switch $SW_1$ and the switch $SW_3$ are turned on and the switch $SW_2$ are left turned off to perform the normal measuring operation. This enables the contaminate particles purge operation.

Figure 26:
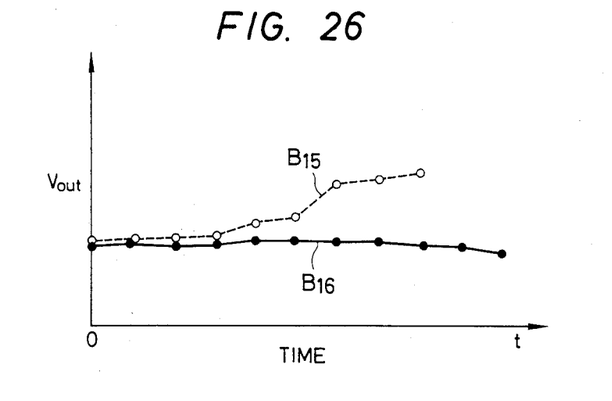
FIG. 26 shows the $V_{out}$ characteristic obtained from an experiment according to the present invention.

FIG. 26 shows the result an experiment using the circuit of FIGS. 23 to 25 during the rich fuel mixture operation. The air-fuel mixture is fixed at a constant ratio. The $V_{out}$ characteristic $B_{15}$ of FIG. 26 is the one shown in FIG. 21 for the engine operation where the contaminate particles purge operation was not performed.

The $V_{out}$ characteristic $B_{16}$ of FIG. 26 is the one which was obtained by using the technique shown in FIGS. 23 to 25. As is seen from FIG. 26, the contaminate particles purge operation oxidizes carbon clearing the diffusion resistor 3 of the clogging carbon particles and ensuring a constant output without drifts.

Figure 27:
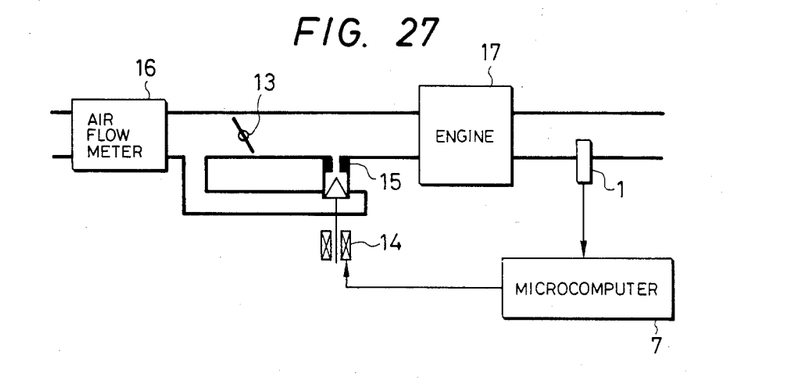
FIG. 27 shows the configuration of the air intake system of the engine.
Figure 28:
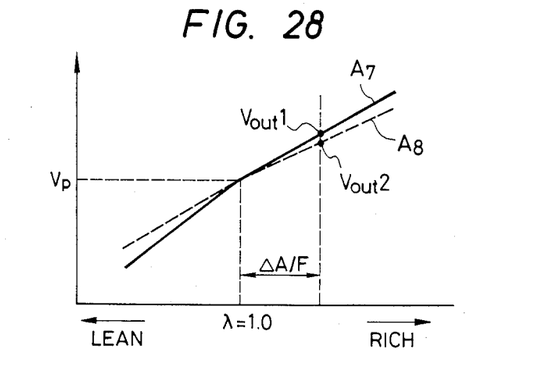
FIG. 28 is a graph showing the relationship between the theoretical air-fuel ratio λ and the $V_{out}$ characteristics.

FIGS. 27 and 28 show the principle of detecting drifts of the air-fuel ratio sensor 1 according to the present invention.

In FIG. 27, during idling of the engine 17 the sonic air is supplied to the engine 17 through the solenoid valve 14 and orifice 15 bypassing the throttle valve 13. An air-flow meter 16 is provided therein. If the bypass air is made to flow at sonic speed, the amount of air supplied (a) is determined only by the opening area of the orifice 15.

Let A and F stand for the amount of air and the amount of fuel getting into the engine 17 when the solenoid valve 14 is off. If the engine 17 is idling at the air-fuel ratio (A/F) of 14.7 with the solenoid valve turned off, the air-fuel ratio when the solenoid valve 14 is off $(A/F)_{OFF}$ is expressed as $$(A/F)_{OFF} = \frac{A}{F} \qquad (7)$$

The air-fuel ratio when the solenoid valve 14 is on $(A/F)_{ON}$ is given by $$(A/F)_{ON} = \frac{A + a}{F} \qquad (8)$$

And their difference ΔA/F is given by $$\Delta(A/F)_{ON} = \frac{A + a}{F} - \frac{A}{F} = \frac{a}{F} \qquad (9)$$

If the amount of fuel F is constant, ΔA/F is also constant. To keep F constant, a closed loop control is performed for λ=1.0 before turning the solenoid valve 14 on. The output $V_{out}$ of the air-fuel ratio sensor 1 for λ=1.0 is the potential ground $V_p$ and there will be no change at all without being affected by the clogging. That is, the value F is always constant and ΔA/F is also constant.

In other words, while the engine 17 is running, the air-fuel ratio A/F is shifted by ΔA/F from time to time to detect the air-fuel ratio sensor drift from the output $V_{out}$. As shown in FIG. 28, when the air-fuel ratio A/F is changed from λ=1.0 by a certain ΔA/F, the sensor output before the characteristic changes occurs is $V_{out}1$ as indicated by a line A7 and the output after drift occurs is $V_{out}2$ as indicated by a line A8. By calculating the difference ($V_{out}1 - V_{out}2$), it is possible to detect the amount of drift accurately.

Figure 29:
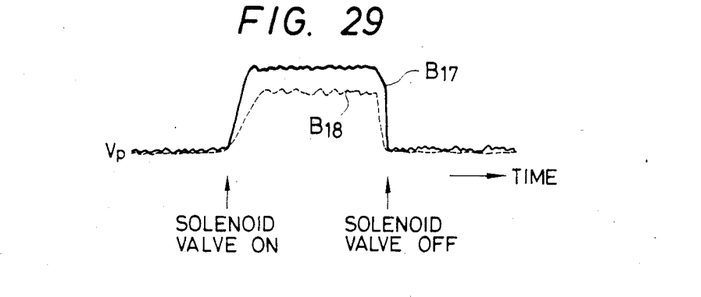
FIG. 29 shows a characteristic obtained from an experiment with the air intake system of FIG. 27.

FIG. 29 shows the result of an experiment illustrating the actual change in the air-fuel ratio A/F during engine operation. The characteristic B17 represents the air-fuel ratio A/F change before drift and B18 the air-fuel ratio A/F change after drift. At first, a closed loop control is performed for the value $V_p$ at the theoretical air-fuel ratio λ=1.0. Then when the solenoid valve 14 is turned on, the outputs change as indicated by $V_{out}1$ and $V_{out}2$. When the solenoid valve 14 is turned off, the sensor outputs return to the original value of $V_p$.

Figure 30:
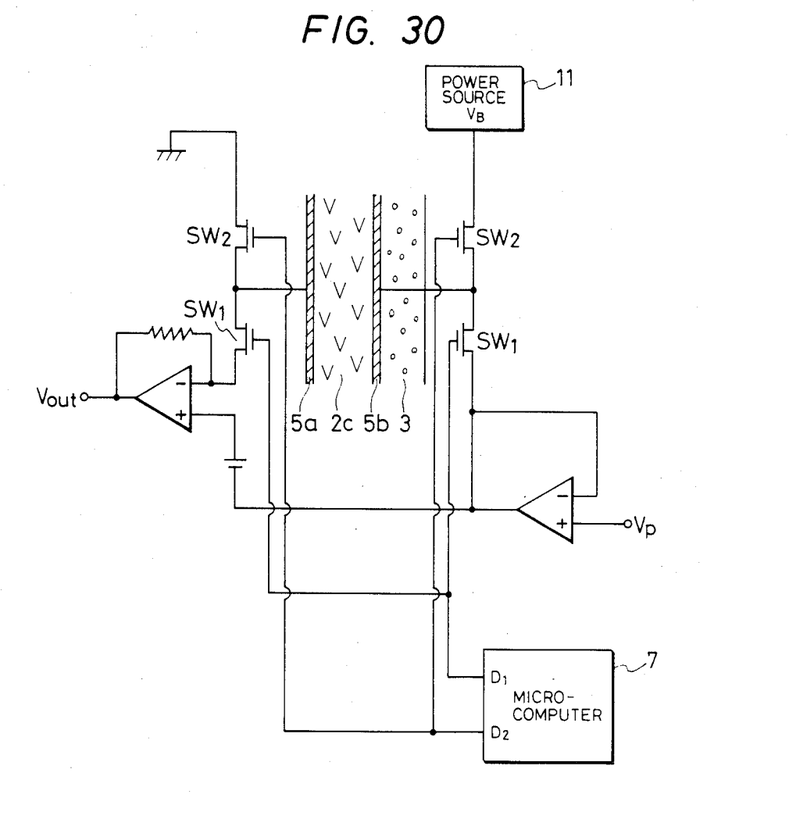
FIG. 30 shows a circuitry having the air-fuel ratio sensor of one embodiment to obtain the $V_{out}$ characteristic of FIG. 29.

FIGS. 29 and 30 show a further embodiment illustrating the circuit and operating process for performing the contaminate particles purge operation after a drift has been detected. This embodiment is based on an idea that the contaminate particles purge operation is carried out only when a drift occurs.

Figure 31:
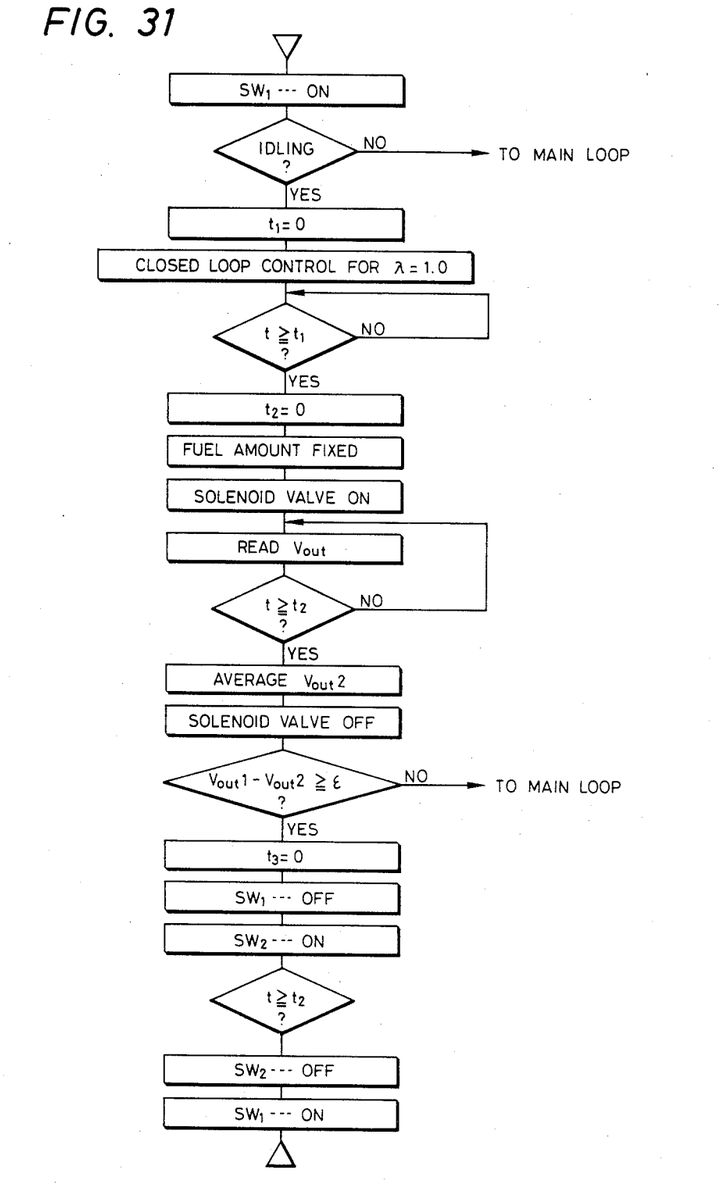
FIG. 31 shows another flow-chart of sensor operation of the air-fuel ratio sensor according to the present invention.

First, a check is made of whether the engine 17 is idling or not. When the engine 17 is idling, a closed loop control is performed at λ=1.0. With elapse of a certain period of time, the value F is fixed and the solenoid valve 14 is turned on. Next, $V_{out}2$ is read for a certain period of time to average the $V_{out}2$, followed by turning off the solenoid valve 14.

When the difference $V_{out}1-V_{out}2$ exceeds a specified value ε, the switch SW1 is turned off and the switch SW2 turned on to cause the oxygen (O2) to flow toward the diffusion resistor 3 by the voltage $V_B$ for a specified duration and thereby oxidize carbon adhering to the diffusion resistor 3. Then, the switch SW2 is turned off and the switch SW1 turned on to return to the normal operation.

We claim:

1. In a method for detecting an air-fuel ratio in an air-fuel ratio detector comprising an oxygen ion conductive solid electrolyte, an exhaust side electrode and an atmosphere side electrode provided on respective sides of the solid electrolyte, a diffusion resistor provided on the atmosphere side electrode and exposed to exhaust gas to be measured, and a heater for heating the diffusion resistor independently of the exhaust gas, wherein the method comprises:

moving the exhaust gas to be measured adjacent the diffusion resistor;

supplying atmosphere, with oxygen, to the solid electrolyte on the side with the atmosphere side electrode;

supplying a current from the atmosphere side electrode to the exhaust side electrode in a sufficient amount at and at sufficient voltage for a measurement period of time and simultaneously determining the air-fuel ratio of the exhaust gas;

supplying current from the exhaust side electrode to said atmosphere side electrode and impressing a voltage across the electrodes during a cleaning period of time sufficiently for moving oxygen from the atmosphere through the solid electrolyte into and through the diffusion resistor to the exhaust gas in an amount and during a time sufficient to oxidize all oxidizable gases within the diffusion resistor and burn off exhaust gas particles adhering to the diffusion resistor;

monitoring the build up of exhaust gas particles on the diffusion resistor and providing a correlated contaminate signal;

comparing the contaminate signal to a reference and providing a cleaning signal when the comparison indicates a contaminate level above a fixed amount; and in response to the cleaning signal, ending the measurement period of time and starting the cleaning period of time.

2. The method according to claim 1, further including:

periodically ending the measurement period of time and starting the cleaning period of time with a period and cleaning period of time sufficient to maintain the diffusion resistor substantially free of contaminates.

3. The method according to claim 1, including heating the diffusion resistor, with the heater, to be within a temperature range of 600 to 900 degrees C during the cleaning period of time.

4. The method according to claim 1, further comprising providing the exhaust side electrode of platinum for providing a catalytic action during the oxidizing of contaminates.

5. In a method for detecting an air-fuel ratio in an air-fuel ratio detector comprising an oxygen ion conductive solid electrolyte, an exhaust side electrode and an atmosphere side electrode provided on respective sides of the solid electrolyte, a diffusion resistor provided on the atmosphere side electrode and exposed to exhaust gas to be measured, and a heater for heating the diffusion resistor independently of the exhaust gas, wherein the method comprises:

moving the exhaust gas to be measured adjacent the diffusion resistor;

supplying atmosphere, with oxygen, to the solid electrolyte on the side with the atmosphere side electrode;

supplying a current from the atmosphere side electrode to the exhaust side electrode in a sufficient amount at and at sufficient voltage for a measurement period of time and simultaneously determining the air-fuel ratio of the exhaust gas;

supplying current from the exhaust side electrode to said atmosphere side electrode and impressing a voltage across the electrodes during a cleaning period of time sufficiently for moving oxygen from the atmosphere through the solid electrolyte into and through the diffusion resistor to the exhaust gas in an amount and during a time sufficient to oxidize all oxidizable gases within the diffusion resistor and burn off exhaust gas particles adhering to the diffusion resistor;

determining when there is a rich fuel mixture operation wherein the air-fuel ratio is substantially smaller than the theoretical air fuel ratio and producing a correlated cleaning signal, and ending the measurement period of time and beginning the cleaning period of time in response to the cleaning signal.

* * * * *